US008957202B2

(12) United States Patent
Wu et al.

(10) Patent No.: US 8,957,202 B2
(45) Date of Patent: Feb. 17, 2015

(54) ENTEROSOLUBLE AND INTESTINAL-ENZYME-BIODEGRADABLE MATERIALS AND METHOD FOR PREPARING THE SAME

(75) Inventors: Chien-Pang Wu, Changhua County (TW); Jyh-Horng Wu, Kaohsiung (TW); Shih-Jung Tsai, Hsinchu (TW); Su-Jane Lo, legal representative, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 394 days.

(21) Appl. No.: 13/437,729

(22) Filed: Apr. 2, 2012

(65) Prior Publication Data

US 2013/0158252 A1 Jun. 20, 2013

(30) Foreign Application Priority Data

Dec. 15, 2011 (TW) .............................. 100146410 A

(51) Int. Cl.
| | | |
|---|---|---|
| *C08B 35/00* | (2006.01) | |
| *C07H 3/06* | (2006.01) | |
| *A61K 47/36* | (2006.01) | |
| *A61K 9/48* | (2006.01) | |
| *C08B 35/02* | (2006.01) | |

(52) U.S. Cl.
CPC . *A61K 47/36* (2013.01); *A61K 9/48* (2013.01); *C08B 35/02* (2013.01)
USPC ..................................................... 536/123.1

(58) Field of Classification Search
CPC ........... A61K 47/36; A61K 9/48; C08B 35/02
USPC ..................................................... 536/123.1
See application file for complete search history.

(56) References Cited

U.S. PATENT DOCUMENTS

| | | | |
|---|---|---|---|
| 4,011,392 A | 3/1977 | Rudolph et al. | |
| 4,079,125 A | 3/1978 | Sipos | |
| 4,095,992 A * | 6/1978 | Rudolph et al. | ............ 106/207.2 |
| 4,138,013 A | 2/1979 | Okajima | |
| 4,365,060 A | 12/1982 | Onda et al. | |
| 5,266,368 A | 11/1993 | Miller | |
| 5,656,292 A | 8/1997 | Urtti et al. | |
| 6,218,532 B1 | 4/2001 | Mark et al. | |
| 6,306,435 B1 | 10/2001 | Chen et al. | |
| 6,331,291 B1 | 12/2001 | Glace et al. | |
| 6,809,074 B2 | 10/2004 | Moe et al. | |

FOREIGN PATENT DOCUMENTS

| | | |
|---|---|---|
| CN | 1117052 A | 2/1996 |
| CN | 1422871 A | 6/2002 |
| CN | 1481253 A | 3/2004 |
| CN | 101974093 A1 | 2/2011 |
| CN | 102086233 A | 6/2011 |
| EP | 1350519 | 8/2003 |
| GB | 1 509 866 | 5/1978 |
| JP | 2002161050 A | 6/2002 |
| JP | 2005239737 A | 9/2005 |
| TW | 246642 | 5/1995 |
| TW | 310277 | 7/1997 |
| TW | 574300 | 2/2004 |
| TW | 200843795 | 11/2008 |
| TW | 200848091 | 12/2008 |
| TW | I304424 | 12/2008 |
| TW | I334355 | 12/2012 |
| WO | WO-0249621 A1 | 6/2002 |

OTHER PUBLICATIONS

Hong-Wei Lu et al., Preparation and properties of new micellar drug carriers based on hydrophobically modified amylopectin, Carbohydrate Polymers, Oct. 7, 2010, pp. 1499-1506, vol. 83.
Yeon-Kye Kim et al., Controlled release of D-glucose from starch granules containing 29% free D-glucose and Eudragit L100-55 as a binding and coating agent, Carbohydrate Research, Mar. 16, 2010, pp. 1065-1067, vol. 345.
Rydell, N. et al., Starch microparticles as vaccine adjuvant, Expert Opinion on Drug Delivery, Sep. 2005, pp. 807-828, vol. 2, Issue 5.
H.X. Guo et al., Amylopectin as a subcoating material improves the acidic resistance of enteric-coated pellets containing a freely soluble drug, International Journal of Pharmaceutics, 2002, pp. 79-86, vol. 235.
Taiwan Office Action for Taiwan Application No. 100146410 dated Aug. 28, 2013.
C. Zhu et al., Preparation of Starch Succinate With Intermediate DS by Aqueous Slurry Reaction, Chinese Journal of Reactive Polymers, 10(2), 2001, pp. 179-185.
China Office Action dated Oct. 10, 2014 from corresponding CN Appl No. 201110455621.5.

\* cited by examiner

*Primary Examiner* — Brandon Fetterolf
*Assistant Examiner* — Yih-Horng Shiao
(74) *Attorney, Agent, or Firm* — Muncy, Geissler, Olds & Lowe, P.C.

(57) ABSTRACT

An enterosoluble and intestinal-enzyme-biodegradable material is provided. The enterosoluble and intestinal-enzyme-biodegradable material includes a modified amylopectin, wherein at least one of hydrogen atoms is replaced by —CO—$(CH_2)_n$—COOH (n is 2-4) and the modified amylopectin has an acid value of 35-180 mg KOH/g. The disclosure also provides a method for preparing an enterosoluble and intestinal-enzyme-biodegradable material.

8 Claims, 3 Drawing Sheets

ENTEROSOLUBLE AND INTESTINAL-ENZYME-BIODEGRADABLE MATERIALS AND METHOD FOR PREPARING THE SAME

CROSS REFERENCE TO RELATED APPLICATIONS

This Application claims priority of Taiwan Patent Application No. 100146410, filed on Dec. 15, 2011, the entirety of which is incorporated by reference herein.

BACKGROUND

1. Technical Field

The technical field relates to an enterosoluble and intestinal-enzyme-biodegradable materials and method for preparing the same.

2. Description of the Related Art

Nowadays, with the development of medicine, various oral drugs and health foods have been developed and launched one after another. In order to avoid active ingredients from being damaged by gastric juice before absorption by the intestine, which lowers therapeutic effect, an oral capsule with an intestine-target function (e.g., enterosoluble capsule) has been developed and research has grown. The traditional preparation of an intestine-targeted capsule material is mainly divided into two kinds of methods: (1) coating synthetic polymers with pH-sensitive properties on a general capsule; and (2) using intestinal-enzyme-biodegradable natural polysaccharide polymer as a capsule material.

SUMMARY

One embodiment provides an enterosoluble and intestinal-enzyme-biodegradable material comprising a modified amylopectin, wherein at least one of hydrogen atoms is replaced by —CO—$(CH_2)_n$—COOH (n is 2-4) and the modified amylopectin has an acid value of 35-180 mg KOH/g or 36-178 mg KOH/g.

One embodiment provides a method for preparing an enterosoluble and intestinal-enzyme-biodegradable material, comprising: providing an amylopectin; providing an anhydride derivative; and mixing the anhydride derivative and the amylopectin to prepare the disclosed enterosoluble and intestinal-enzyme-biodegradable material.

One embodiment provides an enterosoluble and intestinal-enzyme-biodegradable material prepared by the following steps, comprising: providing an amylopectin; and mixing an anhydride derivative and the amylopectin to prepare the disclosed enterosoluble and intestinal-enzyme-biodegradable material.

According to the embodiment, an enterosoluble and intestinal-enzyme-biodegradable material is developed. The enterosoluble and intestinal-enzyme-biodegradable material with pH-sensitive properties is prepared by chemical modification of a natural polysaccharide polymer (e.g., amylopectin) capable of degradation by intestinal enzymes.

A detailed description is given in the following embodiments with reference to the accompanying drawings.

DETAILED DESCRIPTION

Figure 1:
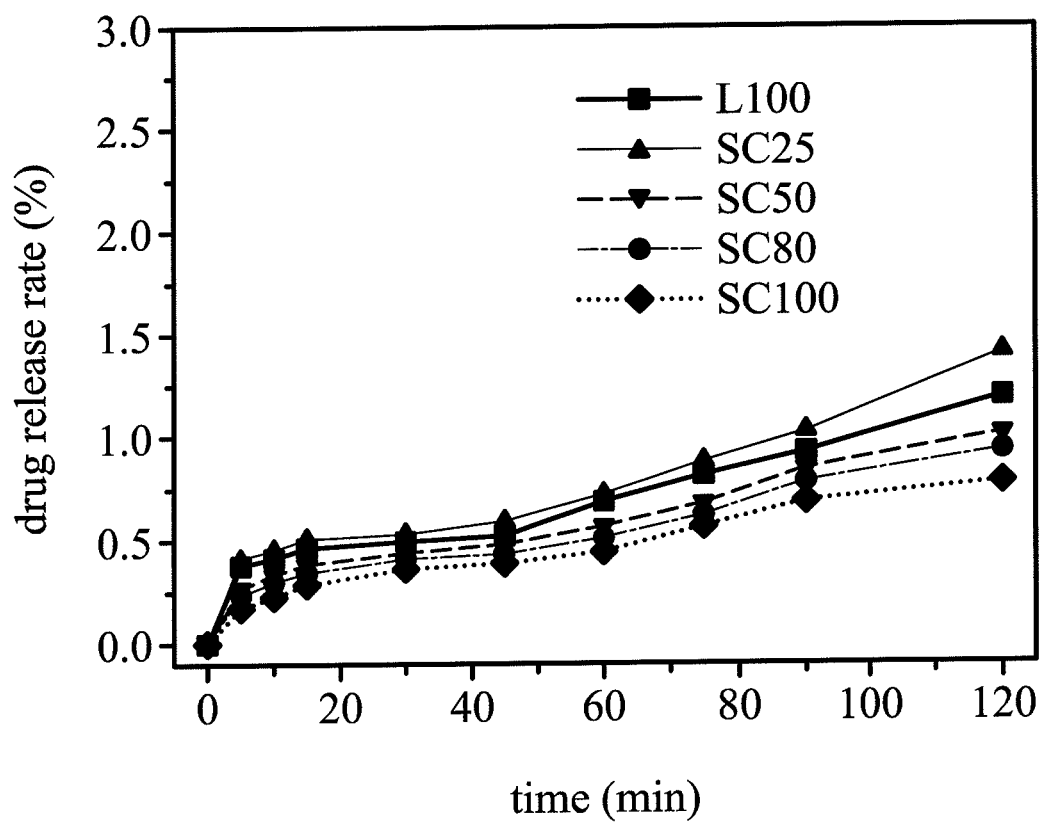
FIG. 1 shows a comparison of the drug release rate between the present modified amylopectin material and a conventional material in a stomach-like environment (pH=1.2) according to an embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment provides an enterosoluble and intestinal-enzyme-biodegradable material comprising a modified amylopectin. In the modified amylopectin, at least one of hydrogen atoms is replaced by —CO—$(CH_2)_n$—COOH (n is 2-4) and the modified amylopectin has an acid value of about 35-180 mg KOH/g or about 36-178 mg KOH/g.

The modified amylopectin has a relative viscosity of about 3.5-16.2 c.p. at 30° C., about 3.2-14.3 c.p. at 40° C., about 2.8-13.2 c.p. at 50° C., about 2.3-10.9 c.p. at 60° C., about 1.9-9.5 c.p. at 70° C. and about 1.76-8.3 c.p. at 80° C.

One embodiment provides a method for preparing an enterosoluble and intestinal-enzyme-biodegradable material, comprising the following steps. An amylopectin and an anhydride derivative are provided. The anhydride derivative and the amylopectin are then mixed to prepare the disclosed enterosoluble and intestinal-enzyme-biodegradable material.

The anhydride derivative and the amylopectin have a molar ratio of about 15:100-100:100 or about 50:100-100:100.

The anhydride derivative may comprise succinic anhydride, glutaric anhydride or adipic anhydride.

The anhydride derivative and the amylopectin are mixed at a temperature of about 90-100° C. for about 10-12 hours.

One embodiment provides an enterosoluble and intestinal-enzyme-biodegradable material prepared by the following steps. An amylopectin is provided. An anhydride derivative and the amylopectin are then mixed to prepare the disclosed enterosoluble and intestinal-enzyme-biodegradable material.

According to the embodiment, an enterosoluble and intestinal-enzyme-biodegradable material is developed. The enterosoluble and intestinal-enzyme-biodegradable material with pH-sensitive properties is prepared by chemical modification of a natural polysaccharide polymer (e.g., amylopectin) capable of degradation by intestinal enzymes. The material can be applied to intestine-targeted capsules which can control the encapsulated drugs used to treat intestinal diseases or health foods which should not to be released under a stomach environment (about pH<3), but released under an intestine environment (about pH>5) and an enzyme environment which achieves the duel intestine-target function. In comparison with traditional intestine-targeted capsule materials, the developed enterosoluble material has the following advantages: (1) it can be dissolved in water to proceed with a capsule-forming process unlike the capsule-forming process of the commercially available enterosoluble material which requires organic solvents; (2) it can better protect the contents therein from being released under a stomach-like acid environment (about pH<3) and (3) it has a higher drug release rate under an intestine-like environment (about pH>5).

Example 1

Preparation of the Modified Amylopectin

First, 15 g of amylopectin (from maize, CAS No.: 9037-22-3) was dried and placed in a four-neck reactor. Dried dimethyl sulfoxide (DMSO) as a solvent was then added to the reactor to prepare an amylopectin solution with a solid content of 5 wt %. Next, the amylopectin solution was stirred using a mechanical agitator at 100° C. under nitrogen gas for 1 hour. The amylopectin was dissolved in DMSO to form a transparent solution. 1.39 g, 1.85 g, 2.32 g, 4.63 g, 7.41 g and 9.27 g of succinic anhydride were then dropped into the solution, respectively, through an isobaric feed pipe and stirred using a mechanical agitator at 100° C. under nitrogen gas for 12 hours to complete the reaction. Various modified amylopectin solutions (SC15, SC20, SC25, SC50, SC80 and SC100) were prepared. Next, a part of the solvent was extracted from the solutions. The solutions were re-precipitated (purified) using ethanol or isopropanol to obtain white powder products. After the products were washed using ethanol or isopropanol for several times, the products were baked in a 60° C. vacuum oven for 24 hours to remove the remaining solvent. The modified amylopectin (SC15, SC20, SC25, SC50, SC80 and SC100) was thus prepared.

Example 2

Acid Value Measurement of the Modified Amylopectin

In accordance with ASTM D974 method, the acid value of the modified amylopectin (SC15, SC20, SC25, SC50, SC80 and SC100) prepared from Example 1 was measured. The results are shown in Table 1.

TABLE 1

| Sample | Acid value (mg KOH/g) |
|---|---|
| Unmodified amylopectin | 4 |
| SC15 | 26 |
| SC20 | 30 |
| SC25 | 36 |
| SC50 | 53 |
| SC80 | 80 |
| SC100 | 178 |

From Table 1, it is shown that the acid value of the unmodified amylopectin was 4 mg KOH/g. The acid value of the modified amylopectin (SC 15) was 26 mg KOH/g. The acid value of the modified amylopectin (SC20) was 30 mg KOH/g. The acid value of the modified amylopectin (SC25) was 36 mg KOH/g. The acid value of the modified amylopectin (SC50) was 53 mg KOH/g. The acid value of the modified amylopectin (SC80) was 80 mg KOH/g. The acid value of the modified amylopectin (SC 100) was 178 mg KOH/g.

Example 3

Enterosolubility Test of the Modified Amylopectin

The enterosolubility of the modified amylopectin prepared from Example 1 was tested under a temperature of 37° C. in accordance with United States Pharmacopeia (USP). The modified amylopectin material was prepared and formed into a thin film, which included the following steps. The modified amylopectin was first dissolved in water to form an amylopectin aqueous solution. The amylopectin aqueous solution was then added to an aluminum dish and dried in a 70-90° C. oven to form a thin film. The thin film was then respectively immersed in a buffer solution with a pH=6.8 (prepared by 0.1N of HCl aqueous solution and 0.2M of $Na_3PO_4$ aqueous solution) and HCl aqueous solution with a pH=1.2 for 12 hours. The results are shown in Table 2.

TABLE 2

| Sample | HCl aqueous solution (pH = 1.2) | Buffer solution (pH = 6.8) |
|---|---|---|
| Unmodified amylopectin | Thin film was disintegrated | Thin film was disintegrated |
| SC15 | Thin film was disintegrated | Thin film was disintegrated |
| SC20 | Thin film was disintegrated | Thin film was disintegrated |
| SC25 | Thin film was intact | Thin film was disintegrated |
| SC50 | Thin film was intact | Thin film was disintegrated |
| SC80 | Thin film was intact | Thin film was disintegrated |
| SC100 | Thin film was intact | Thin film was disintegrated |

From Table 2, after 12 hours, the unmodified amylopectin thin film was disintegrated in both of the HCl aqueous solution and buffer solution. That is, the unmodified amylopectin thin film did not pass through a strong acid environment and serve as an intestine-targeted capsule material. Meanwhile, after immersion in the HCl aqueous solution with a pH=1.2 for 12 hours, the modified amylopectin thin film (SC25, SC50, SC80 and SC100) was still intact. That is, the modified amylopectin thin film can pass through a strong acid environment to serve as an intestine-targeted capsule material. Additionally, after immersion in the buffer solution with a pH=6.8 for 12 hours, the modified amylopectin thin film (SC25, SC50, SC80 and SC 100) disintegrated. That is, the modified amylopectin thin film is enterosoluble.

Example 4

Intestinal-Enzyme-Biodegradability Test of the Modified Amylopectin

In accordance with USP, the intestinal-enzyme-biodegradability of the modified amylopectin prepared from Example 1 was tested. First, the modified amylopectin and α-amylase were added to an aqueous solution with a pH=6.8 under a temperature of 37° C. and stirred for 2 hours to form a solution. 2 ml of the solution was then dropped into a Fehling's solution and heated until boiling. An aldose test of the solution was then performed. If aldose existed in the solution, after heating, the CuO of the Fehling's solution would participate in an oxidation-reduction reaction and then red $Cu_2O$ would precipitate. Thus, the color of the solution can be observed.

Compared to the control group (without addition of α-amylase), both of the unmodified amylopectin and the modified amylopectin (SC 15, SC20, SC25, SC50, SC80 and SC 100) produced a red $Cu_2O$ precipitation. That is, both of the unmodified amylopectin and the modified amylopectin (SC15, SC20, SC25, SC50, SC80 and SC100) can be decomposed by α-amylase, possessing intestinal-enzyme-biodegradability.

Example 5

Drug Release Rate Test of the Modified Amylopectin

In accordance with USP-701, the drug release rate of the modified amylopectin prepared from Example 1 was tested.

Figure 2:
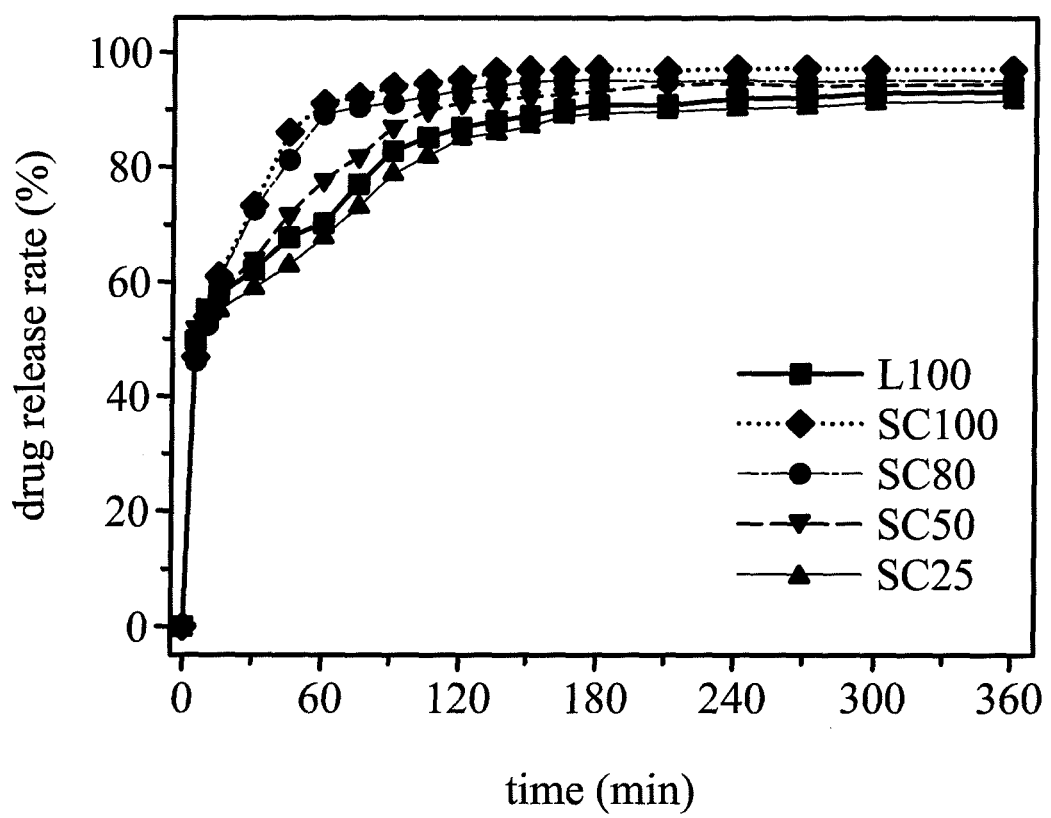
FIG. 2 shows a comparison of the drug release rate between the present modified amylopectin material and a conventional material in an intestine-like environment (pH=6.8, containing α-amylase) according to an embodiment.

First, the prepared modified amylopectin encapsulated with contents was placed in an aqueous solution with a pH=1.2 under a constant temperature of 37° C. for 2 hours. Next, the modified amylopectin was moved to a buffer solution (containing α-amylase) with a pH=6.8 under a constant temperature of 37° C. for 6 hours. During the test, the drug release rate was measured using a UV at different times. The results are shown in FIGS. 1 and 2. From FIG. 1, it is shown that the modified amylopectin (SC50, SC80 and SC100) had a lower drug release rate than that of the commercially available material "Eduragit L100" in a stomach-like environment (pH=1.2). That is, the modified amylopectin can better protect the contents than the "Eduragit L100". The drug release rate of the modified amylopectin (SC25) was similar to that of "Eduragit L100". Additionally, the modified amylopectin (SC50, SC80 and SC100) had a higher drug release rate than that of the "Eduragit L100" within 120 minutes in an intestine-like environment (pH=6.8, containing α-amylase). Also, the drug release rate of the modified amylopectin (SC25) was similar to that of the "Eduragit L100". Even when the test time was extended to 6 hours, the overall drug release rate of the modified amylopectin was still higher than that of the "Eduragit L100". In practical applications, the efficiency of a critical drug can be improved using the modified amylopectin material. In accordance with the test, the present enterosoluble material (SC50, SC80 and SC100) had a better intestine-targeted efficiency than that of the "Eduragit L100".

Example 6

Relative Viscosity Measurement of the Modified Amylopectin

Figure 3:
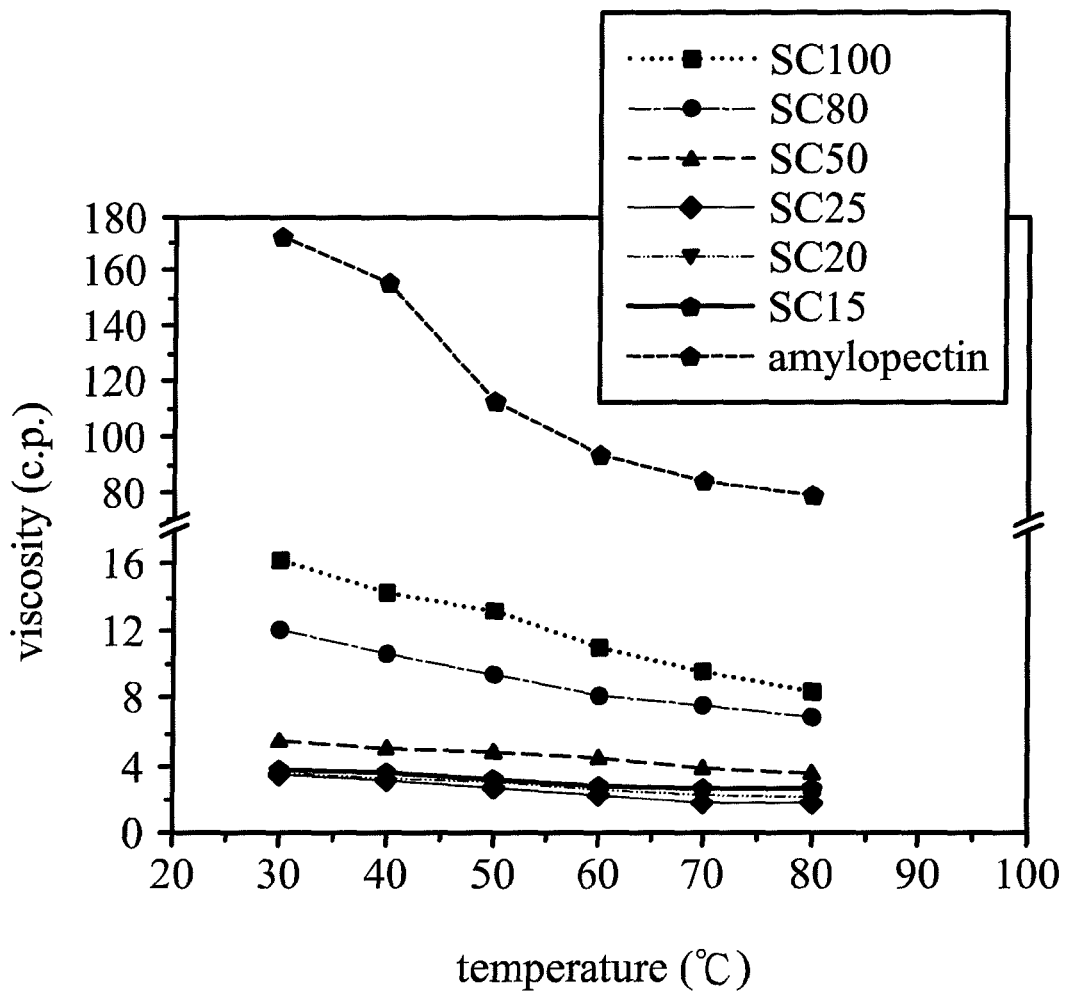
FIG. 3 shows a comparison of relative viscosity between the present modified amylopectin material and a conventional material under various temperatures according to an embodiment.

In accordance with the ASTM D1439 method, the relative viscosity of the modified amylopectin (SC15, SC20, SC25, SC50, SC80 and SC100) prepared from Example 1 was measured. 4 g of the modified amylopectin was dissolved in 100 ml water with heating. After achieving a constant temperature, the relative viscosity of the modified amylopectin (SC15, SC20, SC25, SC50, SC80 and SC100) was measured using a Brookfield viscometer. The results are shown in FIG. 3 and Table 3.

TABLE 3

| Viscosity (c.p.) | SC100 | SC80 | SC50 | SC25 | SC20 | SC15 | Unmodified amylopectin |
|---|---|---|---|---|---|---|---|
| 30° C. | 16.2 | 12.1 | 5.4 | 3.5 | 3.6 | 3.7 | 173 |
| 40° C. | 14.3 | 10.7 | 5.1 | 3.2 | 3.3 | 3.5 | 156 |
| 50° C. | 13.2 | 9.4 | 4.8 | 2.8 | 3.1 | 3.2 | 113 |
| 60° C. | 10.9 | 8.1 | 4.5 | 2.3 | 2.6 | 2.8 | 93 |

TABLE 3-continued

| Viscosity (c.p.) | SC100 | SC80 | SC50 | SC25 | SC20 | SC15 | Unmodified amylopectin |
|---|---|---|---|---|---|---|---|
| 70° C. | 9.5 | 7.6 | 3.9 | 1.9 | 2.3 | 2.7 | 84 |
| 80° C. | 8.3 | 6.8 | 3.6 | 1.76 | 2.1 | 2.6 | 79 |

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for preparing an enterosoluble and intestinal-enzyme-biodegradable material, comprising:
   providing a natural amylopectin;
   providing an anhydride; and
   mixing the anhydride and the amylopectin to prepare an enterosoluble and intestinal-enzyme-biodegradable material having an acid value of 35-180 mg KOH/g, wherein the anhydride and the amylopectin have a molar ratio of 15:100-100:100.

2. The method for preparing an enterosoluble and intestinal-enzyme-biodegradable material as claimed in claim 1, wherein the anhydride and the amylopectin have a molar ratio of 50:100-100:100.

3. The method for preparing an enterosoluble and intestinal-enzyme-biodegradable material as claimed in claim 1, wherein the anhydride comprises succinic anhydride, glutaric anhydride or adipic anhydride.

4. The method for preparing an enterosoluble and intestinal-enzyme-biodegradable material as claimed in claim 1, wherein the anhydride and the amylopectin are mixed at a temperature of 90-100° C.

5. The method for preparing an enterosoluble and intestinal-enzyme-biodegradable material as claimed in claim 1, wherein the anhydride and the amylopectin are mixed for 10-12 hours.

6. An enterosoluble and intestinal-enzyme-biodegradable material prepared by the method as claimed in claim 1 comprising a modified amylopectin, wherein at least one of hydrogen atoms is replaced by —CO—$(CH_2)_n$—COOH (n is 2-4) and the modified amylopectin has an acid value of 35-180 mg KOH/g.

7. The enterosoluble and intestinal-enzyme-biodegradable material as claimed in claim 4, wherein the modified amylopectin has a relative viscosity of 3.5-16.2 c.p. at 30° C.

8. The enterosoluble and intestinal-enzyme-biodegradable material as claimed in claim 4, wherein the modified amylopectin has a relative viscosity of 1.76-8.3 c.p. at 80° C.

* * * * *